(12) United States Patent
Shteren et al.

(10) Patent No.: US 11,636,777 B2
(45) Date of Patent: Apr. 25, 2023

(54) SYSTEM AND METHOD FOR IMPROVING EXERCISE PERFORMANCE USING A MOBILE DEVICE

(71) Applicants: Roy Shteren, Or Yehuda (IL); Shai David, Or Yehuda (IL)

(72) Inventors: Roy Shteren, Or Yehuda (IL); Shai David, Or Yehuda (IL)

( * ) Notice: Subject to any disclaimer, the term of this patent is extended or adjusted under 35 U.S.C. 154(b) by 0 days.

(21) Appl. No.: 17/153,119

(22) Filed: Jan. 20, 2021

(65) Prior Publication Data
US 2021/0225195 A1 Jul. 22, 2021

Related U.S. Application Data

(60) Provisional application No. 62/963,629, filed on Jan. 21, 2020.

(51) Int. Cl.
*G09B 19/00* (2006.01)
*G06T 7/246* (2017.01)
*G16H 20/30* (2018.01)
*G06V 40/20* (2022.01)

(52) U.S. Cl.
CPC ............ *G09B 19/003* (2013.01); *G06T 7/251* (2017.01); *G06V 40/23* (2022.01); *G16H 20/30* (2018.01)

(58) Field of Classification Search
CPC .............. G09B 19/003; G09B 19/0038; G06K 9/00342; G06T 7/251; A63B 24/006; A63B 2024/0068
See application file for complete search history.

(56) References Cited

U.S. PATENT DOCUMENTS

| 10,147,298 | B2 | 12/2018 | Ten Kate | |
| 2017/0177930 | A1* | 6/2017 | Holohan | ................... G06T 7/75 |
| 2017/0326333 | A1 | 11/2017 | Glap et al. | |
| 2019/0046836 | A1* | 2/2019 | Starkey | ................... G01S 17/89 |

(Continued)

FOREIGN PATENT DOCUMENTS

| CN | 103338699 A | 10/2013 |
| EP | 2667776 | 8/2012 |

(Continued)

OTHER PUBLICATIONS

Non-Final Office Action; dated Jan. 21, 2022.

*Primary Examiner* — Peter R Egloff
(74) *Attorney, Agent, or Firm* — David Postolski; Gearhart Law LLC

(57) ABSTRACT

A computing device for implementing a sensor-less method to improve exercise performance is described. An engine of the computing device receives, from a camera of the computing device, video exercise data associated with a user performing an active exercise and then converts the video via a deep learning algorithm to one or more movements of a user's skeleton in real-time performing the active exercise. A first movement of the one or more movements is compared to a predictive model associated with an ideal performance of the first movement. A confidence score is assigned to the comparison. Feedback data is transmitted to a graphical user interface of the computing device for display to the user, where the feedback data includes the confidence score and instructions on how the user can improve the first movement to raise the confidence score.

20 Claims, 9 Drawing Sheets

(56) References Cited

U.S. PATENT DOCUMENTS

| | | | |
|---|---|---|---|
| 2019/0065970 A1 | 2/2019 | Bonutti et al. | |
| 2019/0362139 A1* | 11/2019 | Mehl | A61B 5/486 |
| 2019/0362506 A1* | 11/2019 | Leroyer | G06T 7/97 |
| 2020/0126284 A1* | 4/2020 | Garofalo | G06F 3/017 |
| 2020/0222757 A1* | 7/2020 | Yang | G09B 19/0038 |
| 2021/0004981 A1* | 1/2021 | Song | H04N 5/272 |
| 2021/0154529 A1* | 5/2021 | Barr | G06T 19/006 |

FOREIGN PATENT DOCUMENTS

| | | |
|---|---|---|
| RU | 2603047 C2 | 11/2016 |
| WO | 2012101093 A2 | 8/2012 |
| WO | 2018202731 A1 | 11/2018 |

* cited by examiner

SYSTEM AND METHOD FOR IMPROVING EXERCISE PERFORMANCE USING A MOBILE DEVICE

CROSS-REFERENCE TO RELATED APPLICATIONS

This application is a U.S. Non-Provisional Patent Application that claims priority to U.S. Provisional Patent Application No. 62/963,629, filed on Jan. 21, 2020, the contents of which are hereby fully incorporated by reference.

FIELD OF THE EMBODIMENTS

The field of the invention and its embodiments relate to a method for improving exercise performance. In particular, the present invention and its embodiments provide a computing device and a sensor-less system configured to implement the method for improving exercise performance.

BACKGROUND OF THE EMBODIMENTS

Monitoring of a person's health status, physical ability, and recovery after an injury, hospitalization, or treatment requires extensive face-to-face physician involvement and supervision. Furthermore, prevention of injury requires the aforementioned face-to-face physician involvement and supervision. Monitoring of these factors may be of primary concern in the fields of rehabilitation and physical therapy, neurology and orthopedics, and nursing care. With the increase in technology, the healthcare field has incorporated artificial intelligence (AI) into numerous health services in an attempt to more closely monitor these factors. AI systems may improve health services for the patient, the physician, the physical therapist, and/or the occupational therapist by improving the accuracy of a medical diagnosis, by enhancing an ease by which treatments are managed, and by decreasing the costs of medical services.

AI may even be used in home-based solutions for the remote and real-time monitoring of patients involved in physical therapy and/or rehabilitative efforts. However, these home solutions require dedicated cameras placed around the person's home and/or require the user to wear sensors to capture the movements of the patient. These solutions are expensive, complex to assemble and calibrate, and often require numerous pieces of hardware, generally resulting in a failure to scale. Moreover, these solutions are not user-friendly and may fail to produce accurate results due to their complexity and lack of clinical and research validation.

As the outpatient physical therapy market in the United States, which includes hospitals, rehabilitative centers, assisted living centers, and/or physical therapy providers, among others, is approximately forty billion dollars annually, a reliable home-based solution for the remote monitoring of patients is imperative. Thus, a need exists for an inexpensive and easy-to-assemble system for improving exercise performance. In particular, the present invention and its embodiments provide a sensor-less system for at-home use that utilizes a camera of a computing device to implement a method for improving exercise performance.

Review of Related Technology

U.S. Published Patent Application No. 2019/0065970 A1 describes optimizing and/or personalizing activities for a user through artificial intelligence and/or virtual reality. Generally, the monitoring system comprises at least one monitoring device configured to monitor one or more physical properties of a user and an artificial intelligence (AI) system configured to receive and analyze the monitored physical properties of the user to generate one or more activity parameters optimized or personalized to the user.

CN 103338699 A describes a motion sensing and capture system to track a patient's movements in a physical space to provide patient motion data and/or motion impairment data, which can be used as a diagnostic, predictive or therapeutic tool. After a camera of a computing system captures image data of a patients' movements, a processing system of the computing system produces a patient model and displays a visual rendering of the patient module on a graphical user interface of the computing system. Based on the patient model, physical therapy may be provided to the patient in real-time.

EP 2667776 A0 describes a system for capturing and evaluating motion data of a subject. The system comprises a motion database for selecting a motion appropriate to the subjects initial medical or physical condition, a visual display or audio command to cue a patient to perform the selected motion, an image capture device to capture images of the motions the subject engages in, a processing means to capture a set of data representing the motions the subject engages in, and data analytic software to analyze the set of data to yield a set of values associated with the subject. According to an example in this reference, a camera-controlled computing system may capture patient image data, generate a model of the patient, and display a visual representation of that model in real-time. The system may track the patient in the physical space such that the visual representation maps to the patient or the motion captured in the physical space.

U.S. Pat. No. 10,147,298 B2 generally describes a system for monitoring activities of daily living (ADL) of a person. The system includes: a sensor component that collects sensor signal information regarding the person's motions and activities; an intelligence (or information processing) system that interprets the sensor signal information via artificial intelligence; and a user interface system that enables caregivers to interact with the user.

RU 2603047 C2 describes a contactless system configured to capture and evaluate patient movement data. The system includes a database for selecting a patient movements suitable to the condition of the patient, a visual display to prompt the patient to perform the selected movements, cameras configured to capture images and/or videos of the patient engaging in the selected movements, a processing means for capturing image and/or video data from the captured images and/or videos, and analytical software for analyzing the image and/or video data.

WO 2018/202731 A1 describes a system configured to generate a motion adjustment instruction for a user performing an action. The system comprises: a target module configured to obtain a target biomechanical load distribution for the user, a sensor arrangement configured to monitor the motion of the user so as to obtain monitored motion data, a monitoring module configured to calculate a monitored biomechanical load distribution for the user in accordance with the monitored motion data, an adjustment module configured to calculate a target adjustment to the motion of the user that corresponds to a reduction of a deviation of the monitored biomechanical load distribution from the target biomechanical load distribution, and an instruction module configured to generate a motion adjustment instruction in accordance with the target adjustment.

U.S. Published Patent Application No. 2017/0326333 A1 describes systems and methods for monitoring a patient by positioning the patient for a predetermined medical mission, sensing biometric and physical conditions of a patient during the mission, and displaying a multimedia interaction with the patient to keep the patient in a predetermined position to improve efficacy of a medical mission.

Various references describe attempts at remedying the drawbacks associated with at-home rehabilitative and physical therapy monitoring solutions for patients. The present invention and its embodiments provide a method for improving exercise performance. In particular, the present invention and its embodiments provide a computing device and a sensor-less system configured to implement the method for improving exercise performance.

SUMMARY OF THE EMBODIMENTS

The present invention and its embodiments relate generally a method for improving exercise performance. In particular, the present invention and its embodiments provide a computing device and a sensor-less system configured to implement the method for improving exercise performance.

A first embodiment of the instant invention describes a method executed by a motion analysis engine of a computing device for improving exercise performance. According to the method, the motion analysis engine receives video exercise data captured by a camera of the computing device. The camera may be a two-dimensional (2D) camera or a three-dimensional (3D) camera. The video exercise data is associated with a user performing an active exercise. In some examples, a distance between the user and the camera is approximately three meters when the user is performing the active exercise. Then, the motion analysis engine converts the video exercise data via a deep learning algorithm to one or more movements of a user's skeleton performing the active exercise in real-time.

Next, the motion analysis engine compares a first movement of the one or more movements to a predictive model associated with an ideal performance of the first movement. The motion analysis engine extracts parameters associated with the first movement from an external database (such as a proprietary database and an open-source database) in a post-processing stage. The parameters include: a speed associated with a bone engaging in the first movement, a smoothness associated with the first movement, a continuity associated with the first movement, an effectivity associated with the first movement, a range of motion per body joint, an angle of the bone of the user engaging in the first movement in relation to the camera, an angle of the portion of the bone engaging in the first movement in relation to the camera, an orientation of the bone engaging in the first movement in relation to the camera, and/or an orientation of the portion of the bone engaging in the first movement in relation to the camera, among others.

Then, the motion analysis engine assigns a confidence score to the comparison. The confidence score is calculated for every joint of the user simultaneously. Next, the motion analysis engine transmits feedback data to a graphical user interface of the computing device for display to the user in real-time. The feedback data includes the confidence score and/or instructions on how the user can improve the first movement to raise the confidence score and to more closely match an ideal performance of the first movement from the predictive model.

A second embodiment of the present invention describes a computer system. The computer system includes one or more processors, one or more memories, and one or more computer-readable hardware storage devices. The one or more computer-readable hardware storage devices contain program code executable by the one or more processors via the one or more memories to implement a sensor-less method for improving exercise performance. It should be appreciated that in some examples, the system runs on the cloud. In other examples, the system may be implemented locally on a device. The computer system is used in a facility, such as: a hospital facility, a school facility, a university facility, a sports training facility, a retirement facility, a rehabilitation facility, and/or a fitness facility, among others not explicitly listed herein.

The method includes: receiving video exercise data captured by a camera of the computing device, where the video exercise data is associated with a user performing an active exercise. In some examples, the active exercise of the user is detected by the camera at at least one angle in relation to the computer system. In other examples, the active exercise of the user is detected by the camera at at least two angles in relation to the computer system. It should be appreciated that the active exercise is a physical exercise or a rehabilitative exercise.

The method also includes converting the video exercise data via a deep learning algorithm to one or more movements of a user's skeleton in real-time performing the active exercise. Next, the method includes: comparing a first movement of the one or more movements to a predictive model associated with an ideal performance of the first movement and assigning a confidence score to the comparison. Then, the method includes: transmitting feedback data to a graphical user interface of the computing device for display to the user. The feedback data includes textual data, graphical data, audio data, video data, and/or visual data. The feedback data comprises the confidence store and instructions on how the user can improve the first movement to mirror the ideal performance of the first movement.

In some examples, the method further includes: receiving additional exercise data captured by the camera, identifying the additional exercise data as being associated with the user performing an inactive exercise, and discarding the additional exercise data from analysis.

A third embodiment of the present invention describes a sensor-less method executed by a motion analysis engine of a computing device for improving exercise performance. The sensor-less method includes numerous process steps, such as: receiving video exercise data captured by a camera of the computing device, where the video exercise data is associated with a user performing an active exercise. The method also includes: converting the video via a deep learning algorithm to one or more movements of a user's skeleton in real-time performing the active exercise. Next, the method includes: comparing a first movement of the one or more movements to a predictive model associated with an ideal performance of the first movement, and assigning a confidence score to the comparison. Then, the method includes: transmitting feedback data to a graphical user interface of the computing device for display to the user. The feedback data may include: the confidence score and instructions on how the user can improve the first movement to raise the confidence score.

In general, the present invention succeeds in conferring the following benefits and objectives.

It is an object of the present invention to provide a sensor-less method for improving exercise performance.

It is an object of the present invention to provide real-time guidance to a user for improving exercise performance.

It is an object of the present invention to compare the captured motion with an expected or a predicted motion, create a fitness or confidence score for every joint simultaneously, and provide the patient feedback in real-time, where the feedback includes the fitness or confidence score and clear instructions on what can be improved to increase the score.

It is an object of the present invention to create predefined error settings in a database that will be associated with accuracy instructions on how to improve the performance of the system.

It is an object of the present invention to remove the necessity of face-to-face physical therapy sessions, while ensuring that real-time guidance is provided to a user for improving exercise performance.

It is an object of the present invention to remove the necessity of doctor-supervised physical therapy sessions, while ensuring that real-time guidance is provided to a user for improving exercise performance.

It is an object of the present invention to provide an at-home method for improving exercise performance.

It is an object of the present invention to provide real-time feedback to a user for improving exercise performance.

It is an object of the present invention to provide an inexpensive method for improving exercise performance.

It is an object of the present invention to detect, track, and guide user movements associated with an active exercise via a 2D camera built into a computing device.

DESCRIPTION OF THE PREFERRED EMBODIMENTS

Figure 1:
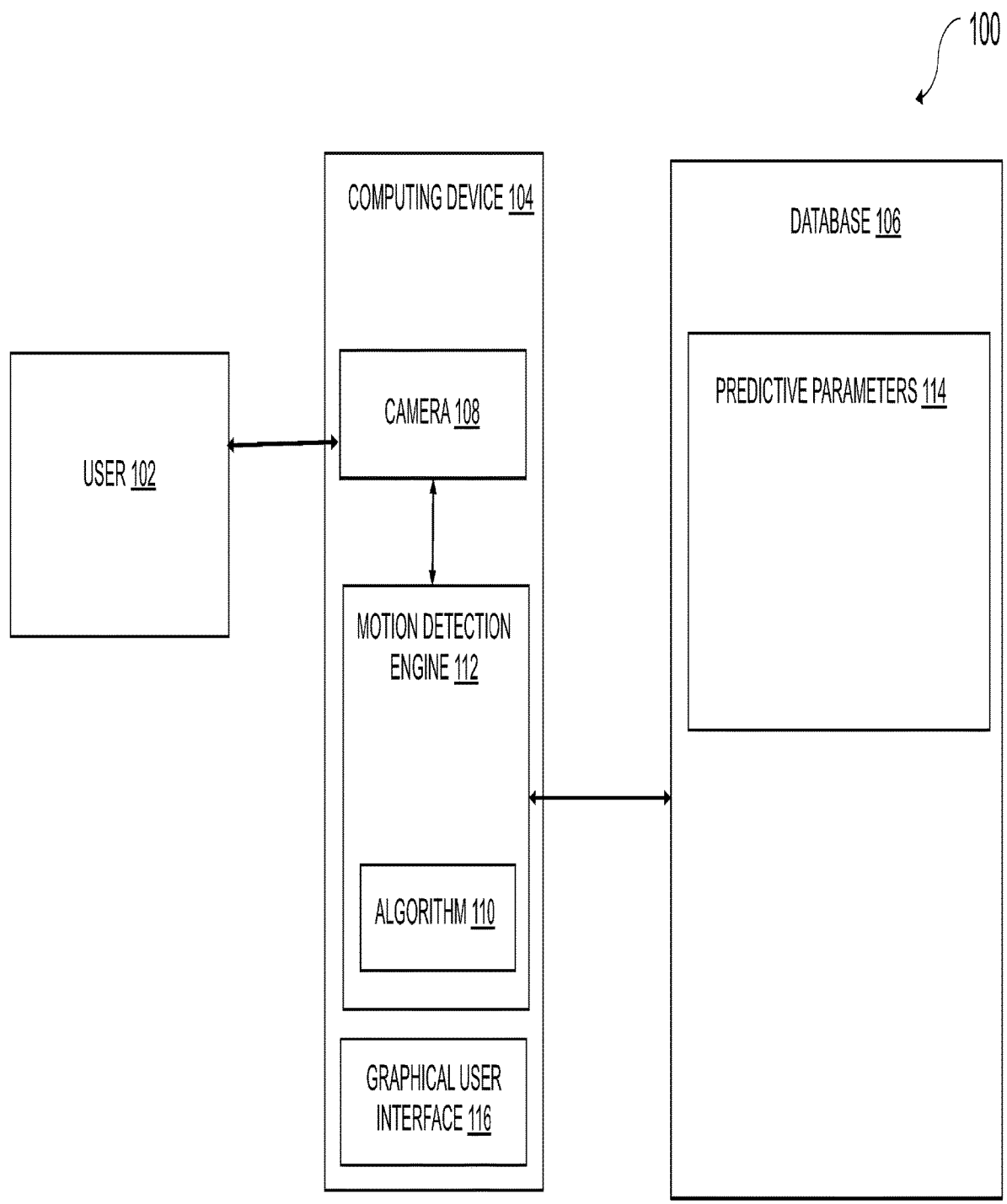
FIG. 1 illustrates a detailed block diagram of a computer system engaging with an external database to execute a method for improving exercise performance, in accordance with embodiments of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 2:
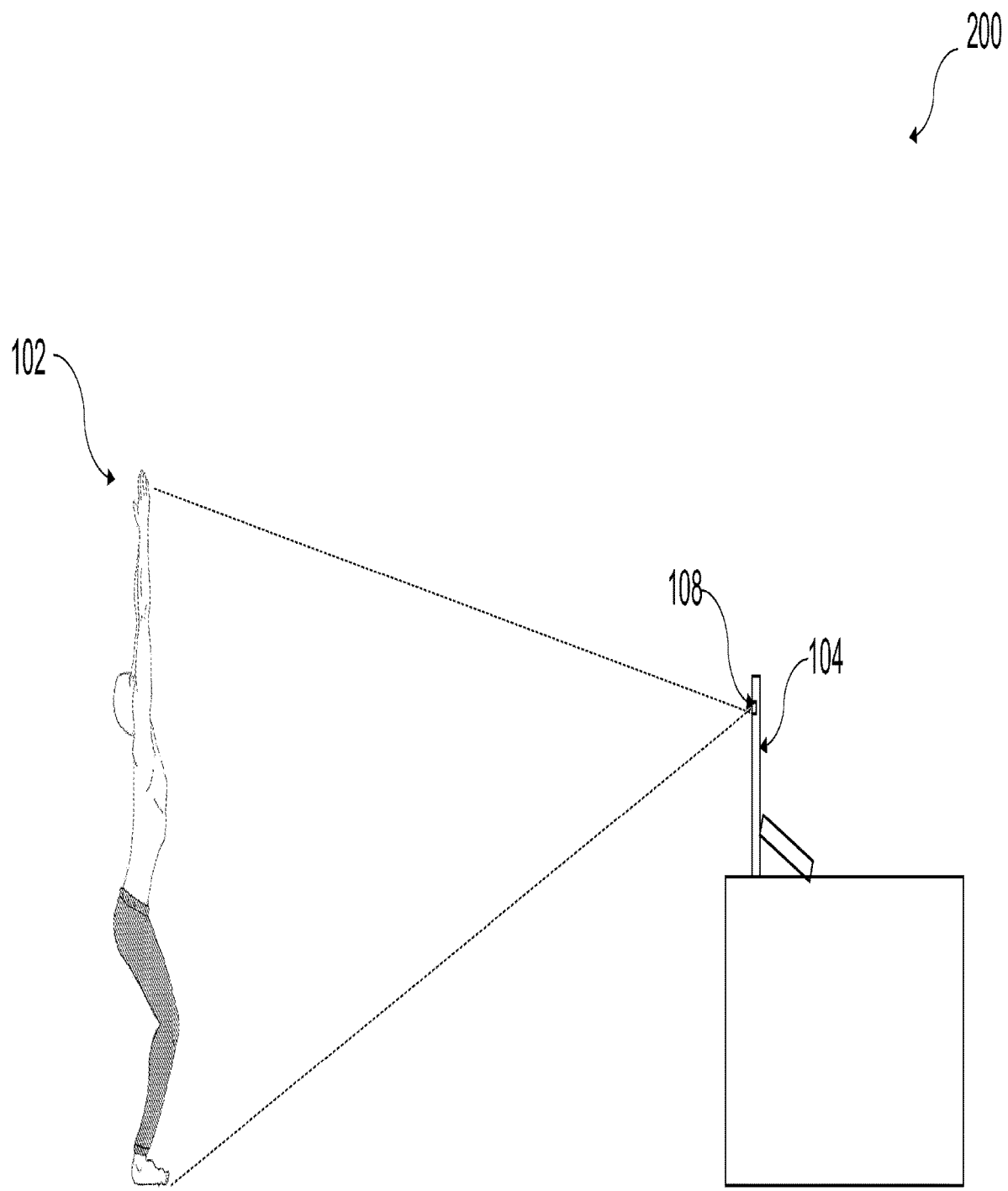
FIG. 2 illustrates use of a computer system configured to execute a method for improving exercise performance, in accordance with embodiments of the present invention.

FIG. 1 illustrates a detailed block diagram of a computer system engaging with an external database to execute a method for improving exercise performance, in accordance with embodiments of the present invention. FIG. 2 illustrates use of a computer system configured to execute a method for improving exercise performance, in accordance with embodiments of the present invention.

According to FIG. 1, a detailed block diagram 100 of a computer system engaging with an external database 106 to execute a method for improving exercise performance is depicted. It should be appreciated that the process steps associated with the method described herein are performed in real-time. The computer system may include a computing device 104, a laptop computer, a smartphone, a desktop computer, or a tablet computer, among others. In examples, the computing device 104 may be used in a facility, such as a hospital facility, a school facility, a university facility, a sports training facility, a retirement facility, a rehabilitation facility, and/or a fitness facility, among other facilities not explicitly listed herein.

The computing device 104 may comprise a camera 108 configured to communicate with a motion analysis engine 112. The motion analysis engine 112 may comprise an algorithm 110 to perform one or more of the process steps described herein. In some examples, the camera 108 may be a two-dimensional (2D) camera. In other examples, the camera 108 may be a three-dimensional (3D) camera. It should be appreciated that the camera 108 may be associated with any mobile computing device, computing device, PC, etc.

In some examples, the algorithm 110 uses geometric computations on the human skeleton. In other examples, the algorithm 110 is trained via wearable sensors that provide 3D motion analysis parameters. An example of a 3D motion analysis parameter is a range of motion parameter. The motion analysis engine 423 may be a motion analysis application or a motion analysis service. In examples, the motion analysis application runs in real-time in the home of the user, where the user does not need to wear any sensors.

In examples, the camera 108 may first capture video exercise data of a user 102. The video exercise data may be associated with the user 102 performing an active exercise, such as a physical exercise (e.g., a balance exercise, a stretching exercise, and/or a flexibility exercise) or a rehabilitative exercise. It should be appreciated that the active exercise is not limited to the examples explicitly described herein. A distance between the user 102 and the camera 108 is approximately three meters when the user 102 is performing the active exercise. Moreover, the camera 108 may capture the video exercise data of the user 102 at at least one angle in relation to the computing device 104. In other examples, the camera 108 may capture the video exercise data of the user 102 at at least two angles in relation to the computing device 104. The camera 108 may then transmit the video exercise data to the motion analysis engine 112.

The active exercise comprises/is an aggregate of one or more movements of the user 102. The motion analysis engine 112 may then convert the video exercise data via a deep learning algorithm to one or more movements of a user's 102 skeleton performing the active exercise in real-time. Assuming the active exercise is a yoga pose, as depicted in FIG. 2, whereby the user 102 places his/her arms directly straight above his/her head and squats low (e.g., the utkatasana pose), the one or more movements may include: the user 102 raising his/her left arm directly straight above his/her head, the user 102 raising his/her right arm directly straight above his/her head, and the user 102 bending his/her knees to squat. When the user 102 is engaging in any one of these movements, the user 102 may be facing the camera 108 directly such that the camera 108 may capture the one or more movements at a 180 degree angle in relation to the user 102. It should be appreciated that the camera 108 of the computing device 104 solely captures the one or more movements associated with the active exercise of the user 102 and the method described herein does not require sensors of any type.

The motion analysis engine 112 may also compare a first movement of the one or more movements to a predictive model associated with an ideal performance of the first movement and may assign a confidence score to the comparison. The confidence score is calculated for every joint of the user 102 simultaneously. In some examples, the confidence score may be in a range of zero to one. For example, a confidence score of 0.7 or 70% would illustrate that the first movement mirrors the predictive/ideal movement by approximately 70%.

Thus, the motion analysis engine 112 can predict a well-performed exercise, as well as detect a wrongly performed exercise. In the case of a wrongly performed exercise (e.g., corresponding to a low confidence score or match), the motion analysis engine 112 may transmit feedback data in real-time to the graphical user interface (GUI) 116 of the computing device 104 for display to instruct the user 102 on how to modify the performed movement to more closely mirror the predicted movement. In an example, the real-time feedback data may include: pre-training improvement instructions, text, sound, etc. Specifically, the feedback data may include the textual data (e.g., one or more explanations on how to modify the first movement to more closely mirror the predictive/ideal movement), graphical data (e.g., one or more pictures depicting how to modify the first movement to more closely mirror the predictive/ideal movement), audio data (e.g., one or more verbal explanations on how to modify the first movement to more closely mirror the predictive/ideal movement), and/or video data (e.g., one or more videos or tutorials on how to modify the first movement to more closely mirror the predictive/ideal movement), etc. Such real-time feedback makes the motion analysis engine 112 function as intelligent as a human physical therapist present with the user 102, though the motion analysis engine 112 utilizes AI and/or software, as well as a 2D or 3D camera embedded in a smartphone or computer.

In a post-processing stage, the motion analysis 112 may extract predictive parameters associated with the first movement from an external database 106 (e.g., an open source database or a propriety database). The predictive parameters 114 associated with the first movement may include: a predicted speed associated with the first movement, a predicted angle of a bone associated with the first movement in relation to the camera 108, a predicted angle of the portion of the bone associated with the first movement in relation to the camera 108, a predicted orientation of the bone associated with the first movement in relation to the camera 108, and/or a predicted orientation of the portion of the bone associated with the first movement in relation to the camera 108, among other examples not explicitly listed herein. Moreover, in an example where the camera 108 is a 2D camera, the predictive parameters 114 may include 2D motion data of a human skeleton performing the first movement. In an alternative example where the camera 108 is a 3D camera, the predictive parameters 114 may include 3D motion data of a human skeleton performing the first movement.

Assuming the first movement is the user 102 raising his/her left arm directly straight above his/her head, parameters associated with this movement may include: a speed associated with a left radius bone, a left ulna bone, and/or a left humerus bone engaging in the first movement; an angle of the left radius bone, the left ulna bone, and/or the left humerus of the user 102 engaging in the first movement in relation to the camera 108; an angle of a portion of the left radius bone, the left ulna bone, and/or the left humerus of the user 102 engaging in the first movement in relation to the camera 108; an orientation of the left radius bone, the left ulna bone, and/or the left humerus of the user 102 engaging in the first movement in relation to the camera 108; and/or an orientation of the portion of the left radius bone, the left ulna bone, and/or the left humerus of the user 102 engaging in the first movement in relation to the camera 108, among other parameters not explicitly listed herein.

In another hypothetical example, assuming the first movement is the user 102 bending his/her knees to squat, the parameters associated with this first movement may include: a speed associated with the user 102 moving from a standing position to a squatting position (which includes a speed associated with the user 102 moving a left femur bone from a vertical position to a horizontal position and a speed associated with the user 102 moving a right femur bone from the vertical position to the horizontal position); an angle of the right femur bone and/or the left femur bone of the user 102 engaging in the first movement in relation to the camera 108; an orientation of the right femur bone and/or the left femur bone of the user 102 engaging in the first movement in relation to the camera 108; and/or an orientation of the portion of the right femur bone and/or the left femur bone of the user 102 engaging in the first movement in relation to the camera 108, among other parameters not explicitly listed herein.

Assuming that the first movement is the user 102 bending his/her knees to squat, as described herein, the predictive parameters 114 associated with the first movement may include: a predicted speed associated with the user 102 moving from a standing position to a squatting position (which includes a speed associated with the user 102 moving the left femur bone from a vertical position to a horizontal position and a speed associated with the user 102 moving the right femur bone from the vertical position to the horizontal position); a predicted angle of the right femur bone and/or the left femur bone of the user 102 engaging in the first movement in relation to the camera 108; a predicted angle of a portion of the right femur bone and/or the left femur bone of the user 102 engaging in the first movement in relation to the camera 108; a predicted orientation of the right femur bone and/or the left femur bone of the user 102 engaging in the first movement in relation to the camera 108; and/or a predicted orientation of the portion of the right femur bone and/or the left femur bone of the user 102 engaging in the first movement in relation to the camera 108, among other examples not explicitly listed herein.

According to FIG. 2, a computer system 200 configured to execute a method for improving exercise performance is depicted. The computer system 200 may include a computing device 104, such as a mobile device. The computing device 104 may comprise a camera 108 configured to communicate with a motion analysis engine 112. In some examples, the camera 108 may be a 2D camera. It should be appreciated that the computer system 200 is substantially similar to the computer system of FIG. 1.

Figure 3:
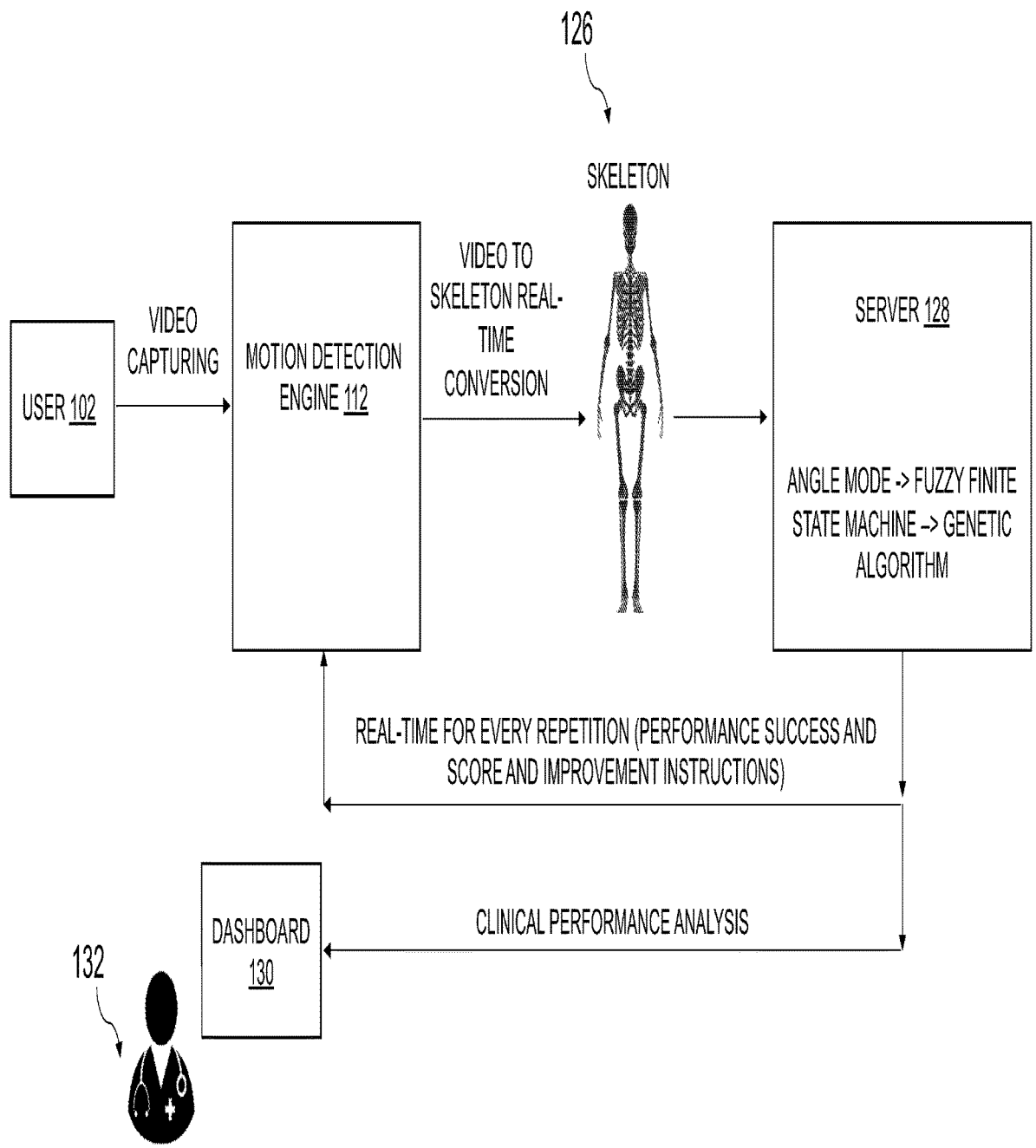
FIG. 3 illustrates a block diagram of a method for improving exercise performance, in accordance with embodiments of the present invention.

FIG. 3 illustrates a block diagram of a method for improving exercise performance, in accordance with embodiments of the present invention.

As shown in FIG. 3, the motion detection engine 112 may capture video of a user performing movement and may convert the video via a third-party deep learning engine (e.g., a computer learning engine) to movement of a user's skeleton 126 in real-time. Such movement may include: a range of motion movement, a sway away from the center of gravity movement, a posture movement, etc. The patient (e.g., the user 102) may also engage in tests that will be later assessed by a clinician 132. The clinician 132 analyzes the users 102 motions and can track the users 102 progress. The tests may include: a Berg balance test, a functional reach test (FRT), a four square step test (FSST), a Tinetti balance test, a timed up and go test, and/or a Romberg test, among others not explicitly listed herein. Then, the motion detection engine 112 may generate an angle model per joint of the user. Such model may be fed to FFSM (e.g., a state machine) and then inserted to a genetic algorithm for optimization.

As described herein, the "Berg balance test" is a widely used clinical test of a person's static and dynamic balance abilities.

As described herein, the "FRT" is a clinical outcome measure and assessment tool for ascertaining dynamic balance in one simple task. In standing, the FRT measures the distance between the length of an outstretched arm in a maximal forward reach, while maintaining a fixed base of support.

As described herein, the "FSST" is used to assess dynamic stability and the ability of the subject to step over low objects forward, sideways, and backward.

As described herein, the "Tinetti balance test" is a test that measures a person's gait and balance.

As described herein, the "Romberg test" is test used in an exam of neurological function for balance, and also as a test for driving under the influence of an intoxicant. The Romberg test is a test of the body's sense of positioning (proprioception), which requires healthy functioning of the dorsal columns of the spinal cord.

The captured video of the user 102 is transmitted to a server 128, such as an artificial intelligence server of FIG. 3. Then, the server 128 utilizes the algorithm 110 described herein to analyze the video captured of the user 102. In some embodiments, the algorithm 110 may analyze the video in real-time for every movement repetition.

Figure 6:
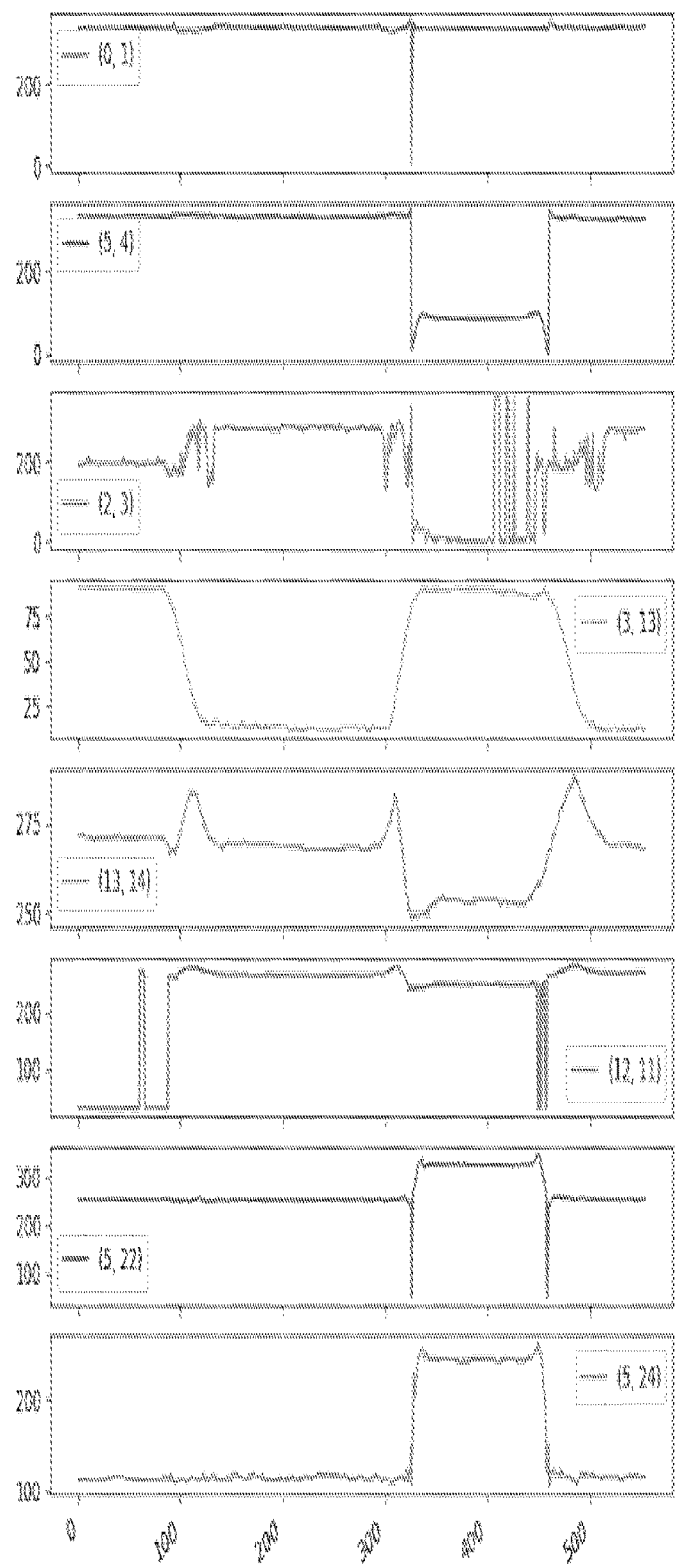
FIG. 6 and FIG. 7 depict graphic representations of angle models per joints calculated with the instant invention, in accordance with embodiments of the present invention.
Figure 7:
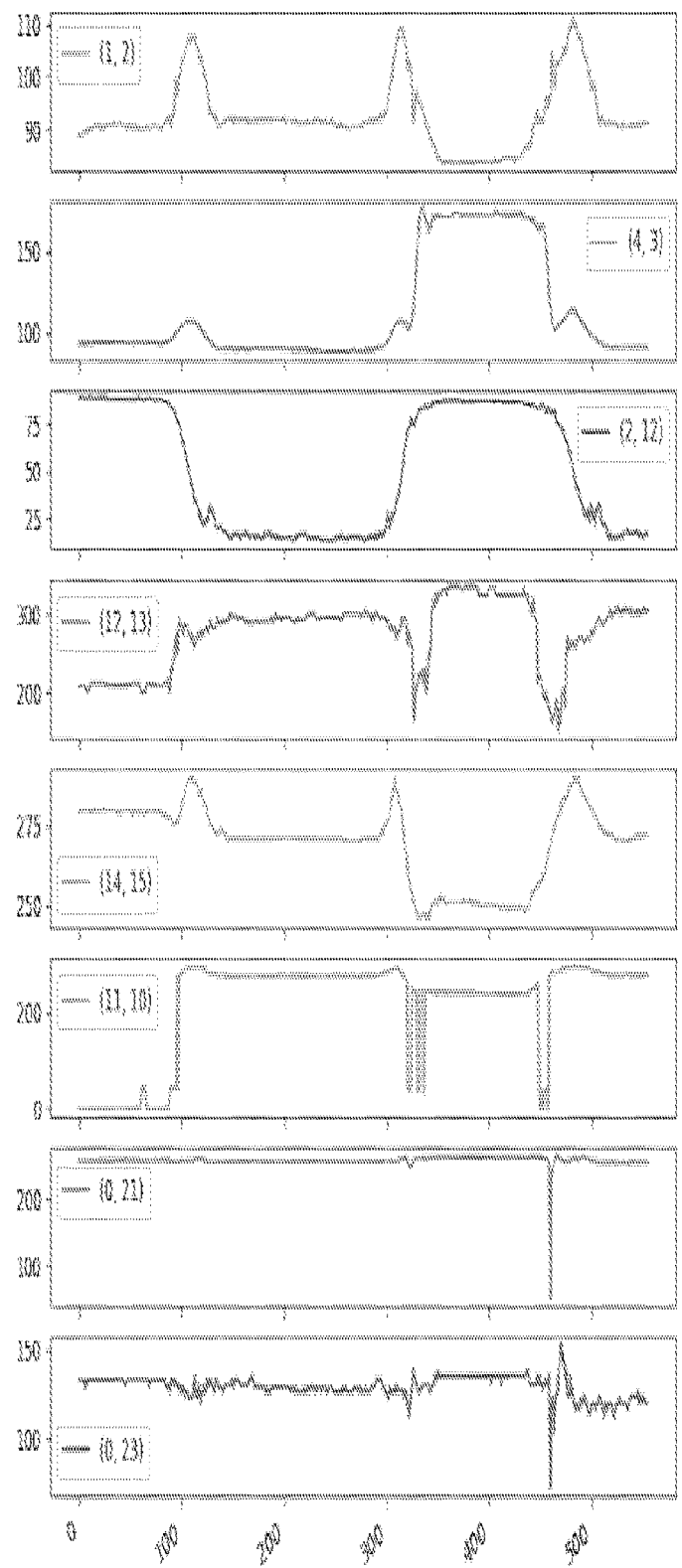

The algorithm 110 may generate results, such as graphical representations of angle models per joint, as shown in FIG. 6 and FIG. 7. Other models for movement may include spatial movement models and/or speed models, among others not explicitly listed herein.

Figure 4:
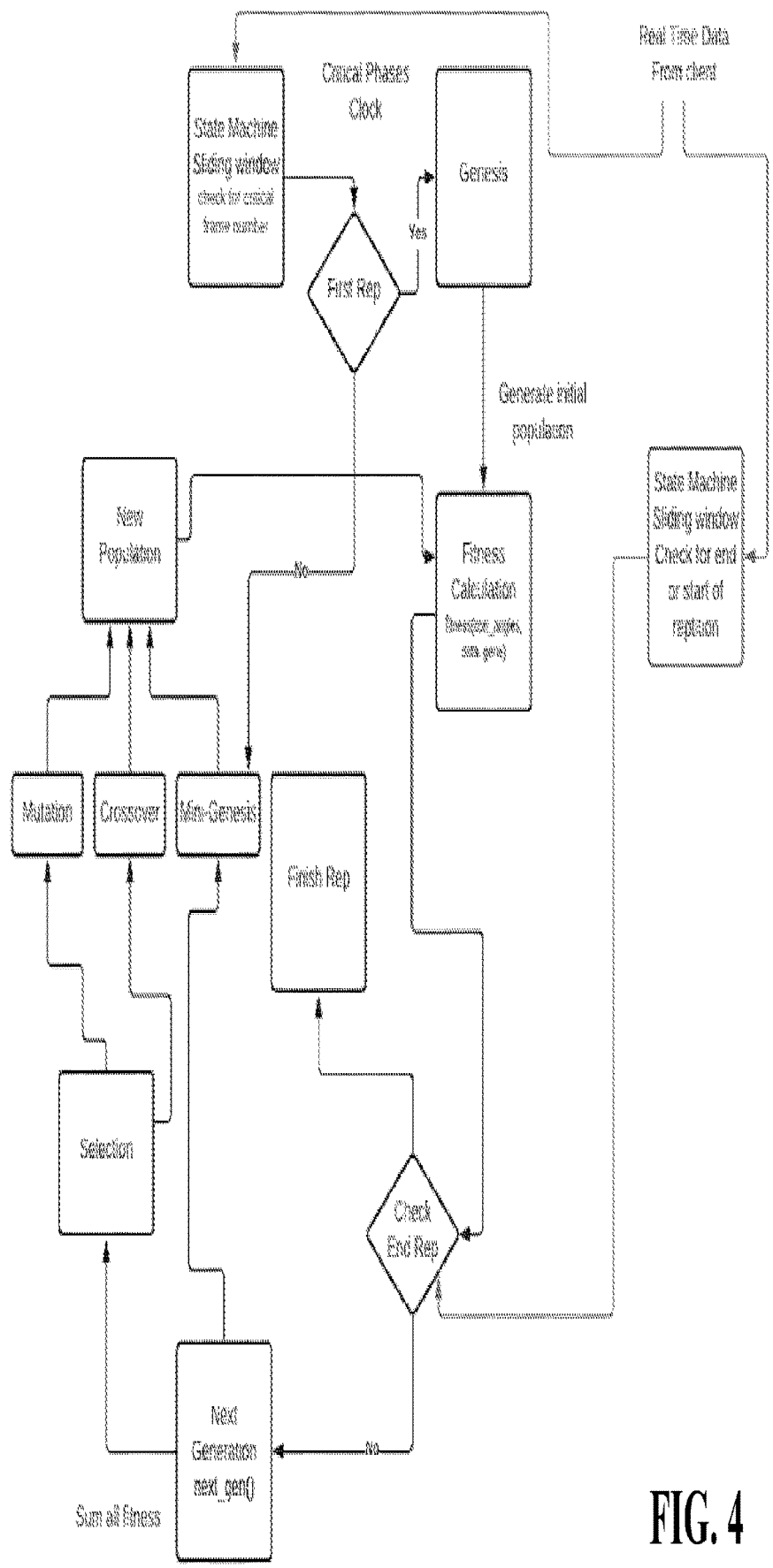
FIG. 4 illustrates a diagram of an algorithmic process associated with a method for improving exercise performance, in accordance with embodiments of the present invention.

The server 128 may transmit the analysis results, performance success results, performance score results, and feedback (e.g., improvement instructions) for every movement repetition back to the motion detection engine 112. Such provides real-time feedback to the patient (e.g., the user 102) via the computing device 104. More specifically, the real-time feedback may include: a fitness score, a score for each repetition, indication of a successful repetition, indication of an unsuccessful repetition, clear instructions on how to improve the next repetition, etc. Further, the server 128 may perform clinical performance analysis on the movement repetitions and may transmit the clinical performance analysis to a dashboard 130 of a computing device for the clinician 132 to review. The clinician 132 may then review the results and/or perform post-processing analysis, which may include: range of motion, speed performance, jerk, symmetric view of performance, and exercise accuracy per repetition. The algorithmic process of the instant invention is depicted explicitly in FIG. 4.

Figure 5A:
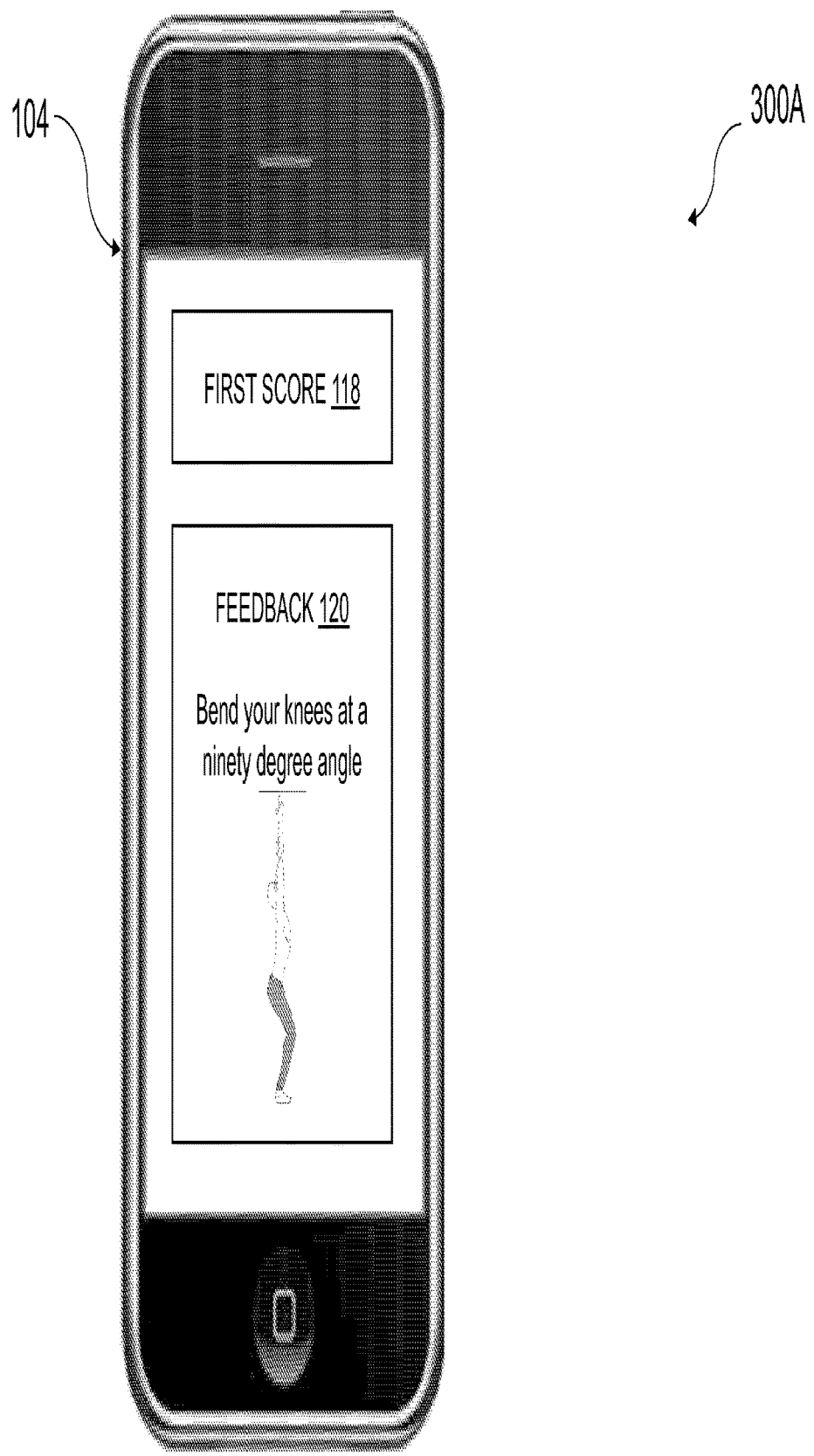
FIG. 5A illustrates a first confidence score and feedback data provided to a computing device of the computer system responsive to execution of a method for improving exercise performance, in accordance with embodiments of the present invention.

FIG. 5A illustrates a first confidence score and feedback data provided to a computing device of the computer system responsive to execution of a method for improving exercise performance, in accordance with embodiments of the present invention.

According to FIG. 5A, a computer system 300A configured to execute a method for improving exercise performance is depicted. FIG. 5A displays a first confidence score 118 and a first set of feedback 120 associated with the first confidence score 118. The first set of feedback 120 may include the textual data (e.g., instructions, such as "bend your knees at a ninety degree angle"), the graphical data (e.g., an image showing proper form of the first movement), the audio data, and/or the video data, that instructs the user 102 on how to modify the first movement to mirror the associated predictive/ideal movement.

Figure 5B:
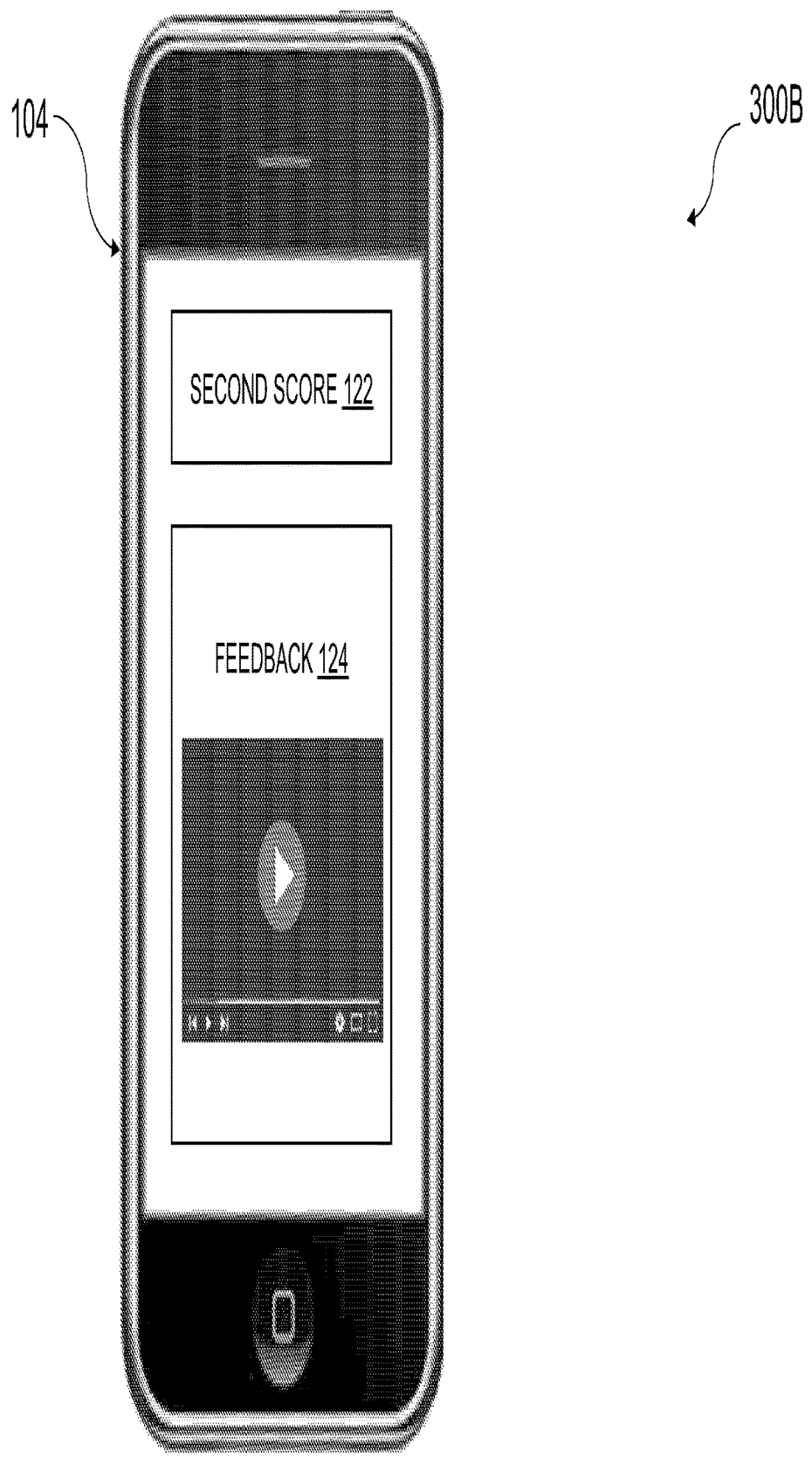
FIG. 5B illustrates a second confidence score and feedback data provided to a computing device of the computer system responsive to execution of a method for improving exercise performance, in accordance with embodiments of the present invention.

FIG. 5B illustrates a second confidence score and feedback data provided to a computing device of the computer system responsive to execution of a method for improving exercise performance, in accordance with embodiments of the present invention.

According to FIG. 5B, a computer system 300B configured to execute a method for improving exercise performance is depicted. FIG. 5B displays a second confidence score 122 and a second set of feedback 124 associated with the second confidence score 122. The second set of feedback data 124 may include the textual data (e.g., one or more explanations on how to modify the movement to more closely mirror the associated predictive/ideal movement), the graphical data (e.g., one or more pictures depicting how to modify the movement to more closely mirror the associated predictive/ideal movement), the audio data (e.g., one or more verbal explanations on how to modify the movement to more closely mirror the associated predictive/ideal movement), and/or the video data (e.g., one or more videos or tutorials on how to modify the movement to more closely mirror the associated predictive/ideal movement), etc.

In some examples where the first confidence score 118 may be greater than the second confidence score 122, the second set of feedback data 124 associated with the second confidence score 122 may be more substantial than the first set of feedback data 120 associated with the first confidence score 118. In some examples, a size, a shape, and a color of the textual data, the graphical data, and/or the visual data will differ based on the confidence score.

In other examples where the first confidence score 118 is greater than the second confidence score 122, the first set of feedback data 120 associated with the first confidence score 118 may include: a larger sized font of the textual data and/or brighter colors (e.g., lighter hues, tints, shades, and/or tones defined by a high color saturation) associated with the textual data, the graphical data, and/or the visual data.

Moreover, since the second confidence score 122 is less than the first confidence score 118, the second set of feedback data 124 associated with the second confidence score 122 may include: a smaller sized font of the textual data and/or darker colors (e.g., darker hues, tints, shades, and/or tones defined by a low color saturation) of the textual data, the graphical data, and/or the visual data. It should be appreciated that both the first set of feedback data 120 and the second set of feedback data 124 may be displayed on the GUI 116 at the same time, or, in alternative examples, may be displayed on the GUI 116 during a first time period and a second time period, respectively.

In other examples where the first confidence score 118 may be less than the second confidence score 122.

Figure 8:
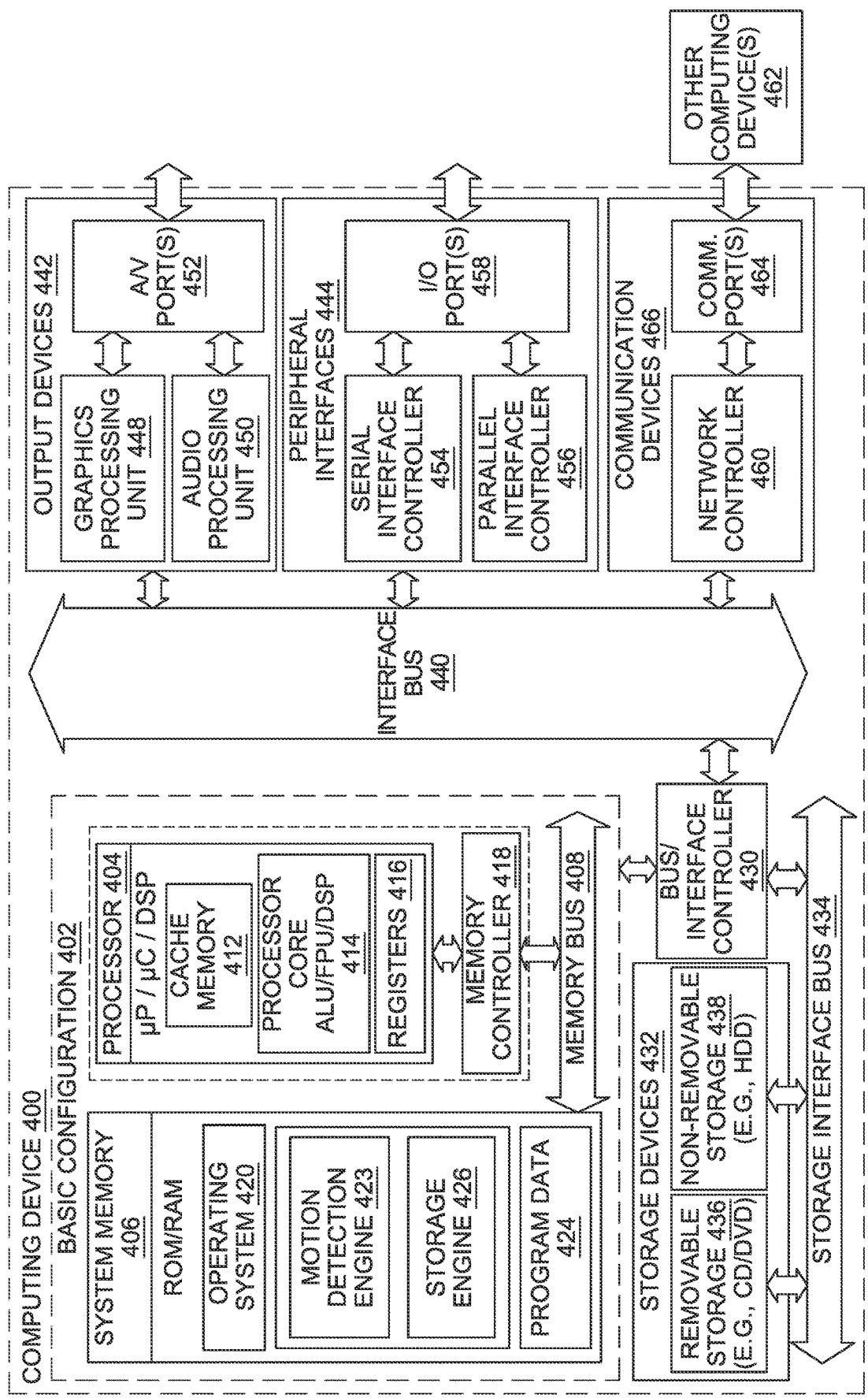
FIG. 8 is a block diagram of a computing device included within the computer system of FIG. 1 configured to execute a method for improving exercise performance, in accordance with embodiments of the present invention.

FIG. 8 is a block diagram of a computing device included within the computer system of FIG. 1 that is configured to improve exercise performance, in accordance with embodiments of the present invention.

In some embodiments, the present invention may be a computer system, a method, and/or a computing device. For example, the computer system and/or the computing device may be utilized to implement a sensor-less method for improving exercise performance. A basic configuration 402 of a computing device 400 is illustrated in FIG. 8 by those components within the inner dashed line. In the basic configuration 402 of the computing device 400, the computing device 400 includes a processor 404 and a system memory 406. In some examples, the computing device 400 may include one or more processors and the system memory 406. A memory bus 408 is used for communicating between the one or more processors 404 and the system memory 406.

Depending on the desired configuration, the processor 404 may be of any type, including, but not limited to, a microprocessor (µP), a microcontroller (µC), and a digital signal processor (DSP), or any combination thereof. Further, the processor 404 may include one more levels of caching, such as a level cache memory 412, a processor core 414, and registers 416, among other examples. The processor core 414 may include an arithmetic logic unit (ALU), a floating point unit (FPU), and/or a digital signal processing core (DSP Core), or any combination thereof. A memory controller 418 may be used with the processor 404, or, in some implementations, the memory controller 418 may be an internal part of the memory controller 404.

Depending on the desired configuration, the system memory 406 may be of any type, including, but not limited to, volatile memory (such as RAM), and/or non-volatile memory (such as ROM, flash memory, etc.), or any combination thereof. The system memory 406 includes an operating system 420, one or more engines, such as a motion analysis engine 423, and program data 424. In some embodiments, the motion analysis engine 423 may be a motion analysis application or a motion analysis service. Moreover, in additional examples, the motion analysis engine 423 may comprise an algorithm, such as an artificial intelligence (AI) computer vision algorithm or a computer vision deep learning algorithm, among other algorithms not explicitly listed herein.

Further, the computing device 400 may comprise a storage engine 426, which may be configured to store information, such as the parameters associated with the first movement, the predictive parameters 114 associated with the first movement and retrieved from the external database 106, the first confidence score 118, the second confidence score 122, the first set of feedback data 120, the second set of feedback data 124, user identifiable information, user diagnosis information, user performance information during a first time period, and/or user performance information during a second time period, among other data not explicitly listed herein. Moreover, in additional examples, the motion analysis engine 423 may generate a user profile housing the information discussed above, such that a doctor, a healthcare provider, and/or the user may track the user's physical or rehabilitative progress.

Moreover, the computing device 400 may have additional features or functionality, and additional interfaces to facilitate communications between the basic configuration 402 and any desired devices and interfaces. For example, a bus/interface controller 430 is used to facilitate communications between the basic configuration 402 and data storage devices 432 via a storage interface bus 434. The data storage devices 432 may be one or more removable storage devices 436, one or more non-removable storage devices 438, or a combination thereof. Examples of the one or more removable storage devices 436 and the one or more non-removable storage devices 438 include magnetic disk devices (such as flexible disk drives and hard-disk drives (HDD)), optical disk drives (such as compact disk (CD) drives or digital versatile disk (DVD) drives), solid state drives (SSD), and tape drives, among others.

In some embodiments, an interface bus 440 facilitates communication from various interface devices (e.g., one or more output devices 442, one or more peripheral interfaces 444, and one or more communication devices 466) to the basic configuration 402 via the bus/interface controller 430. Some of the one or more output devices 442 include a graphics processing unit 448 and an audio processing unit 450, which are configured to communicate to various external devices, such as a display or speakers, via one or more A/V ports 452. The one or more peripheral interfaces 444 may include a serial interface controller 454 or a parallel interface controller 456, which are configured to communicate with external devices, such as input devices (e.g., a keyboard, a mouse, a pen, a voice input device, or a touch input device, etc.) or other peripheral devices (e.g., a printer or a scanner, etc.) via one or more I/O ports 458. Further, the one or more communication devices 466 may include a network controller 460, which is arranged to facilitate communication with one or more other computing devices 462 over a network communication link via one or more communication ports 464. The one or more other computing devices 462 include servers, the database 106, mobile devices, and comparable devices.

The network communication link is an example of a communication media. The communication media are typically embodied by the computer-readable instructions, data structures, program modules, or other data in a modulated data signal, such as a carrier wave or other transport mechanism, and include any information delivery media. A "modulated data signal" is a signal that has one or more of its characteristics set or changed in such a manner as to encode information in the signal. By way of example, and not limitation, the communication media may include wired media (such as a wired network or direct-wired connection) and wireless media (such as acoustic, radio frequency (RF), microwave, infrared (IR), and other wireless media). The term "computer-readable media," as used herein, includes both storage media and communication media.

It should be appreciated that the system memory 406, the one or more removable storage devices 436, and the one or more non-removable storage devices 438 are examples of the computer-readable storage media. The computer-readable storage media is a tangible device that can retain and store instructions (e.g., program code) for use by an instruction execution device (e.g., the computing device 400). Any such, computer storage media is part of the computing device 400.

The computer readable storage media/medium can be a tangible device that can retain and store instructions for use by an instruction execution device. The computer readable storage media/medium may be, for example, but is not limited to, an electronic storage device, a magnetic storage device, an optical storage device, an electromagnetic storage device, and/or a semiconductor storage device, or any suitable combination of the foregoing. A non-exhaustive list of more specific examples of the computer readable storage media/medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and/or a mechanically encoded device (such as punch-cards or raised structures in a groove having instructions recorded thereon), and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Aspects of the present invention are described herein regarding illustrations and/or block diagrams of methods, computer systems, and computing devices according to embodiments of the invention. It will be understood that each block in the block diagrams, and combinations of the blocks, can be implemented by the computer-readable instructions (e.g., the program code).

The computer-readable instructions are provided to the processor 404 of a general purpose computer, special purpose computer, or other programmable data processing apparatus (e.g., the computing device 400) to produce a machine, such that the instructions, which execute via the processor 404 of the computer or other programmable data processing apparatus, create means for implementing the functions/acts specified in the block diagram blocks. These computer-readable instructions are also stored in a computer-readable storage medium that can direct a computer, a programmable data processing apparatus, and/or other devices to function in a particular manner, such that the computer-readable storage medium having instructions stored therein comprises an article of manufacture including instructions, which implement aspects of the functions/acts specified in the block diagram blocks.

The computer-readable instructions (e.g., the program code) are also loaded onto a computer (e.g. the computing device 400), another programmable data processing apparatus, or another device to cause a series of operational steps to be performed on the computer, the other programmable apparatus, or the other device to produce a computer implemented process, such that the instructions, which execute on the computer, the other programmable apparatus, or the other device, implement the functions/acts specified in the block diagram blocks.

Computer readable program instructions described herein can also be downloaded to respective computing/processing devices from a computer readable storage medium or to an external computer or external storage device via a network (e.g., the Internet, a local area network, a wide area network, and/or a wireless network). The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer/computing device, partly on the user's computer/computing device, as a stand-alone software package, partly on the user's computer/computing device and partly on a remote computer/computing device or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to block diagrams of methods, computer systems, and computing devices according to embodiments of the invention. It will be understood that each block and combinations of blocks in the diagrams, can be implemented by the computer readable program instructions.

The block diagrams in the Figures illustrate the architecture, functionality, and operation of possible implementations of computer systems, methods, and computing devices according to various embodiments of the present invention. In this regard, each block in the block diagrams may represent a module, a segment, or a portion of executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block and combinations of blocks can be implemented by special purpose hardware-based systems that perform the specified functions or acts or carry out combinations of special purpose hardware and computer instructions.

Another embodiment of the invention provides a method that performs the process steps on a subscription, advertising, and/or fee basis. That is, a service provider can offer to assist in the method steps of improving exercise performance. In this case, the service provider can create, maintain, and/or support, etc. a computer infrastructure that performs the process steps for one or more customers. In return, the service provider can receive payment from the customer(s) under a subscription and/or fee agreement, and/or the service provider can receive payment from the sale of advertising content to one or more third parties.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method executed by a motion analysis engine of a computing device for improving exercise performance, the method comprising:
   receiving video exercise data captured by a camera of the computing device, the video exercise data being associated with a user performing an active exercise and wearing no sensors;
   converting the video exercise data via a deep learning algorithm to one or more movements of a user's skeleton performing the active exercise in real-time;
   extracting parameters associated with a first movement from an external database in a post-processing stage, wherein the parameters associated with the first movement comprise at least an angle of a bone of the user engaging in the first movement in relation to the camera and an orientation of the bone engaging in the first movement in relation to the camera;
   comparing the first movement of the one or more movements to a predictive model associated with an ideal performance of the first movement;
   assigning a confidence score to the comparison; and
   transmitting feedback data to a graphical user interface of the computing device for display to the user.

2. The method of claim 1, wherein the external database is selected from the group consisting of: a proprietary database and an open-source database.

3. The method of claim 1, wherein the parameters associated with the first movement further comprise at least one of: a speed associated with a bone engaging in the first movement, a smoothness associated with the first movement, a continuity associated with the first movement, an effectivity associated with the first movement, a range of motion per body joint, an angle of the portion of the bone engaging in the first movement in relation to the camera, and an orientation of the portion of the bone engaging in the first movement in relation to the camera.

4. The method of claim 1, wherein the confidence score is calculated for every joint of the user simultaneously.

5. The method of claim 1, wherein the feedback data is transmitted to the user in real-time.

6. The method of claim 1, wherein the feedback data comprises instructions on how the user can improve the first movement to mirror the ideal performance of the first movement.

7. The method of claim 1, wherein the feedback data comprises the confidence score.

8. The method of claim 1, wherein a distance between the user and the camera is approximately three meters when the user is performing the active exercise.

9. The method of claim 1, wherein the active exercise comprises a test selected from the group consisting of: a Berg balance test, a functional reach test (FRT), a four square step test (FSST), a Tinetti balance test, a timed up and go test, and a Romberg test.

10. A computer system comprising one or more processors, one or more memories, and one or more computer-readable hardware storage devices, the one or more computer-readable hardware storage devices containing program code executable by the one or more processors via the one or more memories to implement a sensor-less method for improving exercise performance, the method comprising:
    receiving video exercise data captured by a camera of the computing device, the video exercise data being associated with a user performing an active exercise and wearing no sensors;
    converting the video exercise data via a deep learning algorithm to one or more movements of a user's skeleton performing the active exercise in real-time;
    extracting parameters associated with a first movement of the one or more movements from an external database in a post-processing stage, wherein the parameters associated with the first movement comprise at least an angle of a bone of the user engaging in the first movement in relation to the camera and an orientation of the bone engaging in the first movement in relation to the camera;
    comparing the first movement of the one or more movements to a predictive model associated with an ideal performance of the first movement;
    assigning a confidence score to the comparison; and
    transmitting feedback data to a graphical user interface of the computing device for display to the user.

11. The computer system of claim 10, wherein:
    the feedback data includes textual data, graphical data, audio data, video data, and/or visual data, and
    the feedback data comprises the confidence store and instructions on how the user can improve the first movement to mirror the ideal performance of the first movement.

12. The computer system of claim 10, wherein the active exercise of the user is detected by the camera at at least one angle in relation to the computer system.

13. The computer system of claim 10, wherein the active exercise of the user is detected by the camera at at least two angles in relation to the computer system.

14. The computer system of claim 10, wherein the computer system is used in a facility selected from the group consisting of: a hospital facility, a school facility, a university facility, a sports training facility, a retirement facility, a rehabilitation facility, and a fitness facility.

15. The computer system of claim 10, wherein the method further comprises:
    receiving additional video exercise data captured by the camera;
    identifying the additional video exercise data as being associated with the user performing an inactive exercise; and discarding the additional video exercise data from analysis.

16. The computer system of claim 10, wherein the active exercise is a physical exercise or a rehabilitative exercise.

17. The computer system of claim 10, wherein the active exercise comprises a test selected from the group consisting of: a Berg balance test, a functional reach test (FRT), a four square step test (FSST), a Tinetti balance test, a timed up and go test, and a Romberg test.

18. A sensor-less method executed by a motion analysis engine of a computing device for improving exercise performance, the sensor-less method comprising:
   receiving video exercise data captured by a camera of the computing device, the video exercise data being associated with a user performing an active exercise and wearing no sensors;
   converting the video exercise data via a deep learning algorithm to one or more movements of a user's skeleton performing the active exercise in real-time;
   extracting parameters associated with a first movement from an external database in a post-processing stage, wherein the parameters associated with the first movement comprise at least an angle of a bone of the user engaging in the first movement in relation to the camera and an orientation of the bone engaging in the first movement in relation to the camera;
   comparing the first movement of the one or more movements to a predictive model associated with an ideal performance of the first movement;
   assigning a confidence score to the comparison; and
   transmitting feedback data to a graphical user interface of the computing device for display to the user.

19. The sensor-less method of claim 18, wherein the feedback data comprises the confidence score and instructions on how the user can improve the first movement to raise the confidence score.

20. The sensor-less method of claim 18, wherein the active exercise comprises a test selected from the group consisting of: a Berg balance test, a functional reach test (FRT), a four square step test (FSST), a Tinetti balance test, a timed up and go test, and a Romberg test.

* * * * *